(12) United States Patent
Overes et al.

(10) Patent No.: US 6,425,897 B2
(45) Date of Patent: Jul. 30, 2002

(54) PISTOL FOR THE PRESSING OUT OF BONE CEMENT WITH AN ATTACHABLE CEMENT SYRINGE

(75) Inventors: Tom Overes, Winterthur; Francisco Faoro, Zürich, both of (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/759,555

(22) Filed: Jan. 10, 2001

(30) Foreign Application Priority Data

Jan. 18, 2000 (EP) ............................................ 00810038

(51) Int. Cl.⁷ .............................................. A61B 17/58
(52) U.S. Cl. .......................................... 606/93; 606/92
(58) Field of Search ............................. 606/92, 93, 94, 606/95; 604/57–59, 140, 141, 143, 147; 222/388, 389, 391, 323, 324, 326

(56) References Cited

U.S. PATENT DOCUMENTS

| | | | | |
|---|---|---|---|---|
| 3,768,472 A | * | 10/1973 | Hodosh | 606/93 |
| 4,546,767 A | * | 10/1985 | Smith | 606/93 |
| 5,431,654 A | * | 7/1995 | Nic | 606/92 |
| 5,514,135 A | * | 5/1996 | Earle | 606/93 |
| 6,210,031 B1 | * | 4/2001 | Murray | 366/139 |

FOREIGN PATENT DOCUMENTS

| | | | | |
|---|---|---|---|---|
| DE | 4022986 A1 | | 1/1992 | |
| EP | 0108584 A1 | | 5/1984 | |
| EP | 108584 | * | 5/1984 | 606/93 |
| EP | 0170120 A1 | | 2/1986 | |

* cited by examiner

*Primary Examiner*—Pedro Philogene
(74) *Attorney, Agent, or Firm*—Townsend and Townsend and Crew LLP

(57) ABSTRACT

A pistol for the pressing out of bone cement (1) comprises an attachable cement syringe (2) which has a cylinder (3) with an ejection piston (4) and a narrower neck (5) which adjoins at the cylinder (3), with a displacer bar (6) being insertable into the pistol in order to additionally eject residual cement with a second advance mechanism (8). A first piston (9) acts via a piston rod (7) on the ejection piston (4). A second piston (11), which is displaceably journalled in the piston rod (7) and can be activated independently of the first piston, acts on the displacer bar (6). A fluid (10) which is under pressure is controlled via a control device (12) in such a manner that the displacer bar (6) moves relative to the first piston (9) only when the latter has reached a predetermined end position.

17 Claims, 4 Drawing Sheets

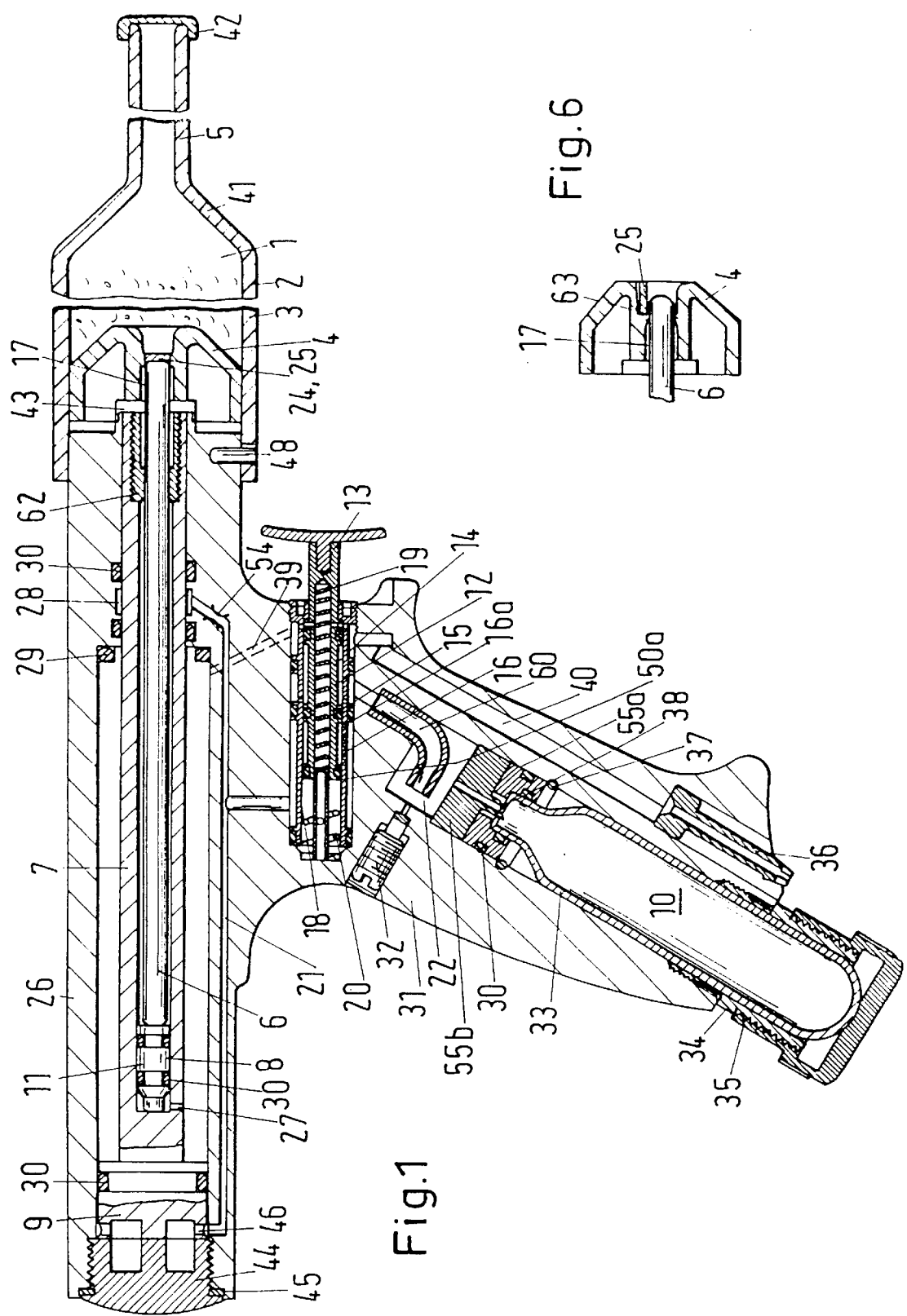

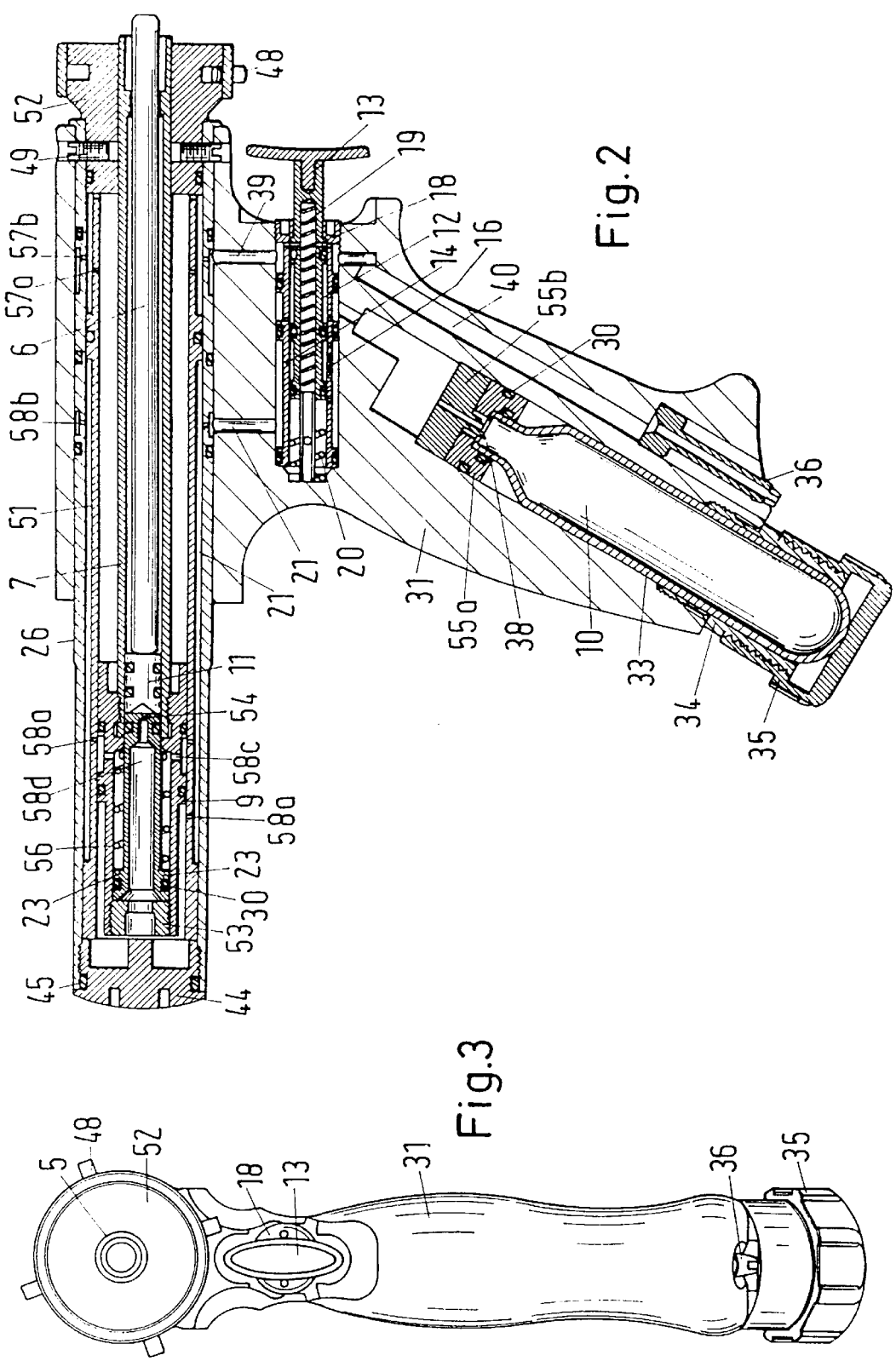

PISTOL FOR THE PRESSING OUT OF BONE CEMENT WITH AN ATTACHABLE CEMENT SYRINGE

Figure 4:
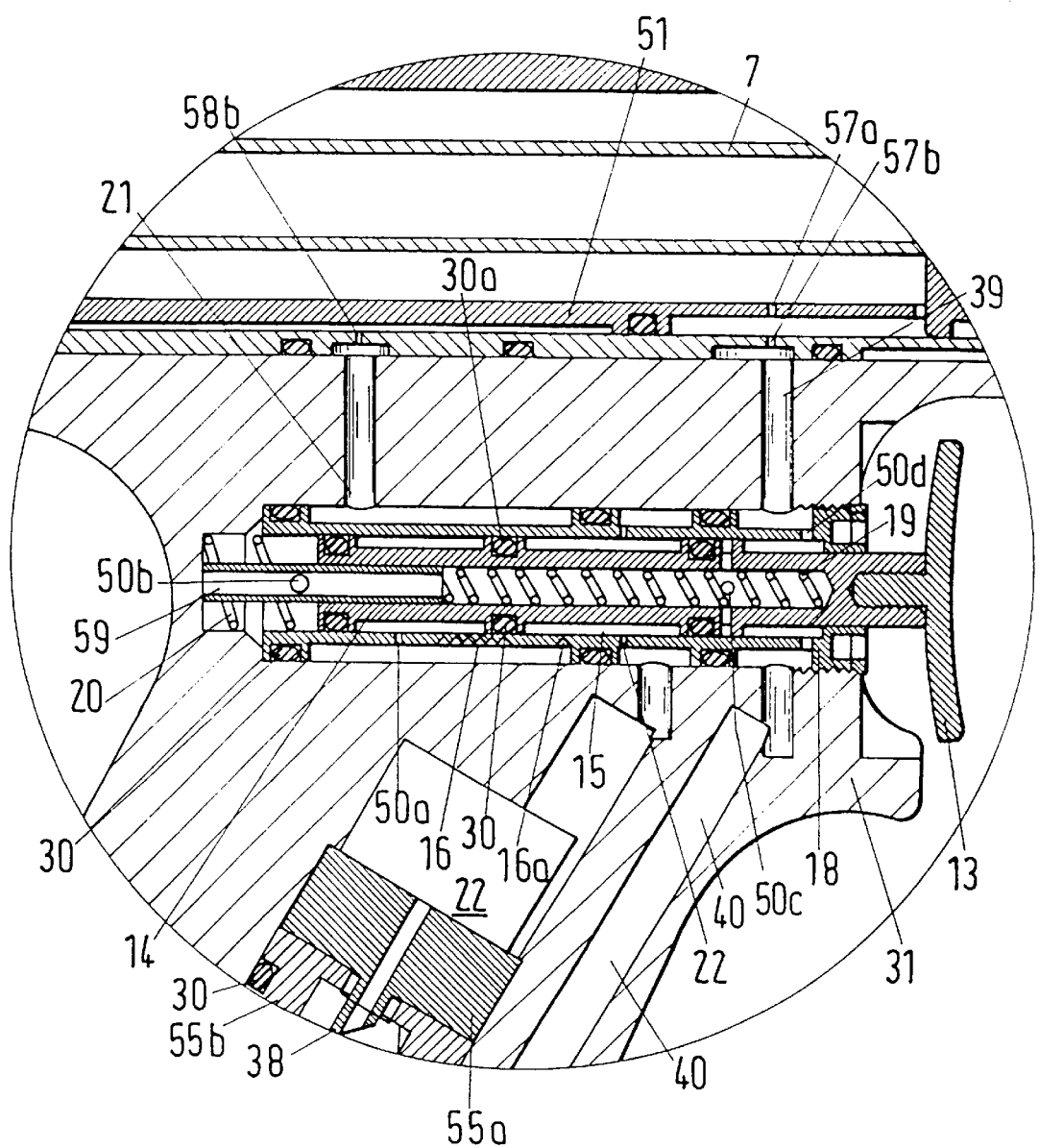

The invention relates to a pistol for the pressing out of bone cement, comprising an attachable cement syringe which has a cylinder with an ejection piston and a narrower neck which adjoins at the cylinder, with a displacer bar being insertable into the pistol, which displacer bar can after the ejection of the cylinder content be introduced into the neck through an aperture of the ejection piston by means of a first tubular bar which acts on the ejection piston and which has second advance mechanism which is journalled in the tubular bar.

Cement pistols for the pressing out of bone cement from a cement syringe have been in use for several years. As a rule the cement syringe is attached to the pistol and then a bar is advanced via a trigger lever against the ejection piston of the cement syringe in order to eject the cement. A ratchet pawl design of this kind is shown in a brochure of the company DePuy, International Ltd., St. Antony's Road, Beeston, Leeds, GB LS11 8DT under the title CMW MKIII ZEMENTPISTOLE (1363-024). It has the special feature that the bar which is actuated via the trigger lever and the ratchet pawl consists of a tube which is provided with a toothing, at the end of which a window is provided. When this window reaches the trigger mechanism the latter grips through the window into the toothing of a further bar which is journalled in the tube and drives this bar further forwards relative to the tube. In cement syringes which have a neck which adjoins at the cylinder the second bar can thus eject the volume in the neck with a displacer bar which is inserted into the tube when the piston which is actuated by the tube has arrived at the end of its path. The apparatus has the disadvantage that it is unwieldy because the two bars project rearwardly by their full length at the beginning of the ejection. A further disadvantage is that the operator must perform the pressing out work by hand. Even though the movement of the bars is stepped down by the trigger lever he must nevertheless actuate the latter many times.

In the patent specification U.S. Pat. No. 5,514,135 a throw-away bone cement syringe with an integrated pistol grip and a $CO_2$ cartridge which is provided in the grip is shown. A small pressure chamber is displaced with the trigger lever from the $CO_2$ side to the charging side of a free piston in order to supply compressed $CO_2$ portion-wise to the piston. The bone cement is filled in through a closeable opening which is provided in the jacket surface of the cement syringe and can be ejected after the closing of this opening via a further outlet opening. A disadvantage of this arrangement consists in that it must be sterilizable with respect to the choice of materials, but can be used only once. A further disadvantage consists in that there exists here the risk of a non recognizable gas breakthrough to the bone cement when the piston binds and/or its sealing ring fails with respect to gas tightness. A gas breakthrough is not tolerable even in small amounts.

The object of the invention is to create an easy to handle cement pistol which is suitable for different ejection conditions. This object is satisfied in accordance with patent claim 1 in that the tubular bar is designed as a piston rod of a first piston which is charged in the pistol by a fluid; and in that the second advance mechanism has a second piston which is charged by the fluid and which ejects the displacer bar, with the two pistons being excitable with the fluid, which is under pressure, via a control device in the pistol.

Advantageous further developments of the invention result through the subordinate claims 2 to 14.

In order to determine the feasibility of a versatilely usable pistol for the pressing out of bone cement, in particular for compressible gaseous fluids, experiments were required.

For a cement syringe with a long attached neck, as is used in the "retrograde" filling up of a thigh bone marrow chamber, for example the following data resulted:

| Waiting time after the stirring of the bone cement [min] | 6:00 | 6:20 | 5:38 | 4:00 |
|---|---|---|---|---|
| Temperature [° C.] | 24.4 | 20.0 | 19.5 | 20.2 |
| Average ejection force [N] | 750 | 700 | 650 | 500 |
| Outflow speed [mm/s] | 2.2 | 5.6 | 7.5 | 10.0 |

For a cement syringe with a short neck, such as is used in the "antegrade" filling up of a bone cavity, for example the following data resulted:

| Waiting time after the stirring of the bone cement [min] | 3:15 | 5:30 |
|---|---|---|
| Temperature [° C.] | 20 | 20 |
| Ejection force [N] | 130 | 240 |
| Outflow speed [mm/s] | 10 | 10 |

For the pressing out of the bone cement out of a long attached neck with a displacer bar there resulted for example a force of 25 Newtons.

The control device and both the first and the second piston, which are charged by fluid, are arranged and dimensioned such that the above ejection conditions can be fulfilled. The fluid can be a liquid or a gas. These can be conducted to the pistol grip and away again externally via hoses. The handling becomes simpler when the reservoir with the fluid is integrated into the pistol for example in the form of gas cartridges in the grip part. $CO_2$ cartridges have the advantage that the fluid can be introduced as a liquid with the cartridge and takes up little volume. In addition the pressure in the reservoir does not fall off too rapidly as long as liquid $CO_2$ is still present.

The invention has the advantage that the operator can concentrate fully on the actual cement application. In addition the device can be used for different cement syringes, i.e. with necks of different lengths and with or without a displacer bar.

Furthermore, it is necessary that the ejection movement of the second piston be initiated only when the first piston has brought the ejection piston into its end position. In a triggering of the second piston which is too early, the latter would close off the outflow in the neck of the cement syringe via the displacer bar. A solution provides for using the displacer bar itself as a restoring mechanism. When the stroke of the first piston is greater than the possible displacement path of the ejection piston and an end-side gap between the piston rod and the ejection piston is present, the full ejection force between the displacer bar and the ejection piston can be produced over the width of this gap. This ejection force suffices in order to push a membrane or flap which is arranged in the passage opening for the displacer bar to one side with the displacer bar and to push the latter with the second piston further into the neck. If no displacer bar is inserted, the second piston admittedly necessarily receives a charging by the fluid in the end position of the first piston, but it moves only slowly up to an abutment in accordance with a restrictor point lying therebefore.

In another solution the second piston is charged from the very beginning with the fluid which is under pressure and the displacer bar, which itself is supported by the membrane at the ejection piston, prevents the second piston from moving relative to the first piston. This causes the resistance of the membrane to puncturing to be significantly greater than the greatest pressing out force during the pressing out of the bone cement from the cylindrical part of the cement syringe and the maximum force which can be produced in the encountering of the ejection piston with the transition piece to the neck of the cement syringe to be significantly greater than the resistance of the membrane.

A further possibility of producing a breaking-loose force at the displacer bar consists in a differential piston between the first and the second piston, with the differential piston taking up the pressure from the fluid over a short path with its additional piston surface and transferring this additional force directly to the second piston, which in turn moves the displacer bar.

The controlling of the fluid flow advantageously takes place with a trigger bow which is connected to a control slider.

With a fluid which enters in gas form into the control device it is difficult to use a conventional control slider since due to the low advance speeds for the ejection piston the restrictor points for the fluid flow must be chosen so small that the influence of the clearance of the control slider acts disturbingly. It therefore proved advantageous to journal a control slider with O-rings in a tube piece and to place a blocking region and individual bores in this tube piece in the longitudinal direction at such a spacing from one another that they are freed for the through-flow one after the other by an O-ring in the control slider. Since in a gas cushion which is present at the piston under pressure, the former continues to be present and to press out cement even when the through-flow of the infeed line is blocked, it is advantageous when the gas cushion which is still present is simultaneously compulsorily ventilated when the trigger bow is not actuated, i.e. when the infeed is blocked.

In order to provide the operator with a tactile feel for the pressing-out speed, he must first bring the trigger bow out of the blocking region against a weak spring into a slow pace region in which a small single bore becomes free as a through-flow cross-section. For $CO_2$ this bore diameter can amount to 0.08 mm in order after the attaching of the cement syringe to move the bone cement slowly and in a preparatory manner up to the opening of the syringe. During the further pulling through of the trigger bow a stiffer spring comes into engagement; at the same time the number of the effective individual bores is increased. In this way it is possible to distribute the functions of blocking, slow pace and pressing out up to maximum speed over a displacement path of the trigger bow which can amount to between 10 and 20 mm and which is felt to be pleasant for the setting.

Figure 5:
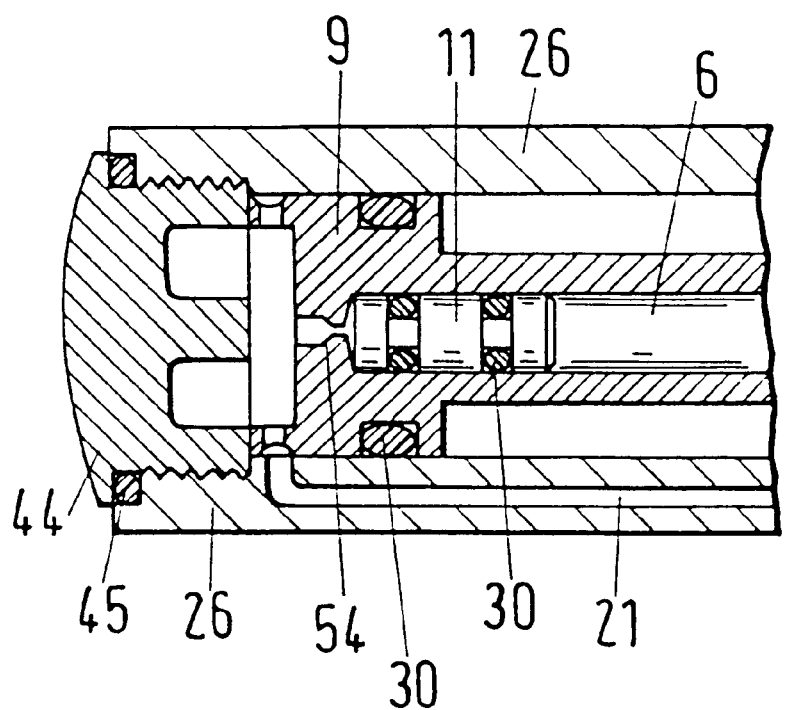

In the following the invention will be described with reference to exemplary embodiments. Shown are:

FIG. 1 schematically, a longitudinal section through a cement pistol with cement syringe attached;

FIG. 2 schematically, a longitudinal section through a further arrangement with an additional differential piston;

FIG. 3 schematically, a front view of FIG. 2;

FIG. 4 schematically, an enlarged section of the control device of FIG. 2 in which the trigger lever is at slow pace;

FIG. 5 schematically, an enlarged section analogous to FIG. 1 with a second piston which is charged by the fluid at the same time as the first piston;

FIG. 6 schematically, a section of FIG. 1 with a flap in the aperture of the ejection piston which is opened by the displacer bar.

The figures show a pistol for the pressing out of bone cement 1 with an attachable cement syringe 2 which has a cylinder 3 with an ejection piston 4 and a narrower neck 5 which adjoins at the cylinder 3, with a displacer bar 6 being insertable into the pistol in order to additionally eject residual cement with a second advance mechanism 8. A first piston 9 acts via a piston rod 7 on the ejection piston 4. A second piston 11, which is displaceably journalled in the piston rod 7, acts on the displacer bar 6. A fluid 10 which is under pressure is controlled via a control device 12 in such a manner that the displacer bar 6 moves relative to the first piston 9 only when the latter has reached a predetermined end position.

In the figures the same reference symbols are use for similar functional elements. Thus O-rings are provided in general with the reference symbol 30.

In the example of FIG. 1 a cement syringe 2 which is filled with liquid bone cement 1 is closed off at its neck 5 with a cap 42. At its opposite side the cement syringe 2 is closed off at a cylinder 3 with an ejection piston 4, which in turn has an aperture 17 which is closed off with a membrane 24 or flap 25. The cylinder 3 is secured with a bayonet lock via pins 48 at the housing 26 of the cement pistol. A first piston 9 is displaceable in the housing 26 in the ejection direction. Its stroke is limited in a rear end position through a cover 44 and in a front end position through a buffer 29. The ejection movement of the first piston 9 is transferred to a piston rod 7, which has at the same time a longitudinal bore in which a second piston 11 is held in its rear end position through an inserted displacer bar 6. The other end of the displacer bar 6 protrudes out of the piston rod 7 into an aperture 17 of the ejection piston 4 and has contact with a membrane 24 or a flap 25, which covers off the aperture 17.

Between the end side of the piston rod 7 and the ejection piston 4 there is a gap 43. In an ejection movement of the first piston 9 the displacer bar 6 first strikes against the membrane 24 or a flap 25 in the aperture 17 of the ejection piston 4, opens the aperture 17 and closes it off at the same time with its cross-section. If the resistance of the membrane 24 or of the flap 25 is too great, the aperture 17 is first punctured when the ejection piston 4 encounters a conical transition 41 of the cement syringe 2. The stroke of the first piston 9 is dimensioned such that it reaches its front end position only when the gap 43 has been eliminated and the aperture 17 has been punctured. In FIG. 7 a flap 25 is secured with a film hinge 63 in the aperture 17 of the ejection piston 4 and can be opened by the displacer bar 6 with a relatively low axial force. A closure of the aperture 17 in the form of a membrane 24 or a flap 25 is obligatory only when work is carried out with the same arrangement without a displacer bar 6 as well. In such a case a stopper in the aperture 17 would also suffice as a closure.

When the first piston 9 has reached its front end position and the aperture 17 of the ejection piston has been punctured by the displacer bar 6, a radial bore 27 of the piston rod 7 which leads behind the second piston 11 in its rear end position has reached a ring space 28 in the housing 26 which is sealed off via O-rings 30. This ring space 28 is likewise fed via the fluid 10 which is under pressure, with a restrictor point 54 determining the fluid flow and thus the advancing speed of the displacer bar 6 when it dips into the neck 5 of the cement syringe. With or without the displacer bar 6 the second piston 11 moves up to a front abutment 62, which is designed as a sleeve which can be screwed in.

After the pressing out of the bone cement the cement syringe 2 and the displacer bar 6 can be removed from the cement pistol, and the second and the first piston 11, 9 can be thrust back into their rear end position. Depending on the capacity of the pressure source for the fluid 10 a new displacer bar 6 and a new bone cement syringe 2 can immediately be attached to the pistol.

Connected up to the housing 26 is a grip part 31 in which a cartridge 33 with a fluid 10, for example $CO_2$, which is under pressure, a control device 12 and a connection 36 for transporting off the used fluid are provided. The cartridge 33 is held in its position via an insert 34 and a holding nut 35. Two ring pieces 55a, 55b are held with a snap ring 37 in the grip part. The ring piece 55a seals with O-rings between the neck of the cartridge 33 and the grip part 31. The ring piece 55b pierces with a hollow cutter 38 a closure film of the cartridge 33 and liberates the fluid. The fluid first enters into an inflow line 22 which is expanded in the case of $CO_2$ to form an antechamber into which a bent tubelet 60 protrudes. This has the advantage that even when the pistol is pointed vertically downwards the $CO_2$, which emerges in liquid form from the cartridge 33, evaporates in the antechamber and is fed in as gas to the control device 12 without fluid residues entering into the control device 12. The antechamber can be ventilated prior to the removal of the cartridge 33 with a ventilation screw 32.

The actual control device will be described later with FIG. 4. The fluid enters after the control device 12 into a connection line 21 and from there arrives via a bore 46 at the first piston 9 and via the restrictor point 54 and the ring space 28 at the piston rod 7. The space before the first piston 9 up to the piston rod 7 is ventilated via a return line 39 through the control device 12 to a return line 40 so that no pressure which moves the second piston 11 through the bore 27 can build up. Only when the bore 27 has reached the ring space 28 does the fluid arrive at the second piston 11.

FIG. 5 shows a variant of FIG. 1 in which a ring space 28 is dispensed with and in which the second piston 11 is fed directly through the first piston 9 via a restrictor point 54. This causes the displacer bar 6 not to break through the ejection piston 4 during the ejection of bone cement out of the cylinder 3 of the cement syringe. For this reason a membrane 24 would have to be dimensioned relatively strongly. A further solution with a membrane 24 which is to be dimensioned weakly is shown in FIG. 2.

In FIGS. 2 and 3 the housing 26 and the grip part 31 are separated and connected via bolts 49 which at the same time fix a head part 52 which carries the pins 48 for the actual bayonet lock of a cement syringe 2. Between a cover 44, which is sealed off against the housing 26 with a seal 45, and the head part 52 a separate cylinder 51 is captured in which a first piston 9 runs, the piston rod 7 of which projects out of the head part 52 in order to act directly on an ejection piston 4. A second piston 11 is journalled in the hollow piston rod 7 and can act on an insertable displacer bar 6. From the very beginning this second piston 11 is, with the first piston 9, under the pressure of the fluid which is fed in from the control device 12 via connection lines 21 and bores 58a, 58b to the first piston 9 and further via a restrictor point 54 to the second piston 11. The cross-section of the second piston 11 is relatively low so that a membrane 24 in the ejection piston 4 which blocks the second piston 11 via the displacer bar 6 may be dimensioned to be relatively weak, since it is supported on the opposite side by the bone cement which is under the pressing-out pressure.

A differential piston 23 is arranged inside the first piston 11 and corresponds with its smaller piston to the diameter of the second piston 11, which protrudes into the hollow piston rod 7 and which contains the restrictor point 54 to the second piston 11. The differential piston 23 is pressed by a spring 56 into its rear end position against a ruptured closure screw 53. Since the differential piston 23 is surrounded on all sides with the same high pressure of the fluid, it maintains this end position in the first piston 9 as long as the pressure relationships do not change. Only when the first piston 9, which ejects the ejection piston 4 directly via the piston rod 7, has reached its front end position do the pressure relationships change, since a bore 58c is short circuited via bores 57a and 57b with a pressure-less return line 39. Bores 58d in the smaller diameter of the differential piston 23 are dimensioned to be so small that the pressure in the ring space falls off ahead of the differential piston through the ventilation. The differential piston 23 is therefore ejected in accordance with the pressure difference on the ring surface in the ejection direction and produces at the second piston 11 an additional force, which is sufficient in order to puncture the membrane 24 with the displacer bar 6. The piston surface of the second piston 11 is sufficient for the subsequent dipping in of the displacer bar 6 into a neck 5 of a cement syringe 2.

Analogously to FIG. 1 a cartridge 33 for a fluid 10 is built in into the grip part 31, likewise a return line 40 with a connector 36. The control device 12 is the same as in the example of FIG. 1 and will be described in the following.

The enlarged illustration in FIG. 4 shows the control device 12. A tube piece 18 is built in in the grip part 31 and guides on its inner side a control slider 14 which is provided with a trigger bow 13. The tube piece 18 is subdivided into different zones on its outer side through O-rings 30. A first zone is connected to the return line 40. A further, second zone is connected to the inflow line 22 and a third zone is connected to the connection line 21 for the pistons 9, 11. On the inner side of the tube piece 18 the control slider 14 forms with O-rings 30 two displaceable chambers to the tube piece 18, which are separated by an O-ring 30a which forms a kind of control edge. Along the tube piece 18. there is for this O-ring 30a a blocking region 15 without a bore in the jacket surface, bordering on the latter a single bore 16a for a slow pace and following the latter at a distance a plurality of individual bores 16. When the control slider 14 is not actuated it is held through a first, weak restoring spring 19 in its extreme right position, in which the O-ring 30a separates the inflow line 22 from the connection line 21. When the trigger bow 13 is actuated the individual bore 16a for the slow pace is first freed, with the cross-section of the individual bore co-determining the pressing out speed of the ejection piston 4 or of the displacer bar 6. For a $CO_2$ cartridge the diameter of the individual bore 16a amounts to 0.08 mm.

When the trigger bow 13 is moved further, the position which is drawn in FIG. 4 arises, in which further individual bores 16 are freed, with a greater ejection speed arising through the growth of the passage surfaces. The advantage of this device consists in that through the O-rings 30, 30a practically no clearance losses arise, and that in spite of the smaller cross-sections the growth of the passage surface can be distributed over a longer path, which can be ideally matched to the movement range of a trigger finger. A further tactile aid is a second restoring spring 20, which additionally comes into engagement during the transition from the individual bore 16a to the further individual bores 16 and thus provides a feel for the size of the passage cross-section or for the ejection speed respectively. In FIG. 2 the control slider 14 is drawn in its extreme right position. In this "unactuated" position, bores 50c and 50d become congruent so that the inner space in which the first restoring spring 19 is journalled is ventilated to the return line 40. At the same time the connection line 21 is connected via bores 50a and 50b to this inner space in this position and is likewise ventilated. This has the result for the operator that in every interruption of the pressing out process the pressure cushion between the control slider 14 and the pistons 9, 11 is depleted in order to prevent an inadvertent subsequent pressing.

What is claimed is:

1. Pistol for the pressing out of bone cement, comprising an attachable cement syringe which has a cylinder with an ejection piston and a narrower neck which adjoins at the cylinder, with a displacer bar being insertable into the pistol, which displacer bar can after the ejection of the cylinder content be introduced into the neck through an aperture of the ejection piston by means of a first tubular bar which acts on the ejection piston and which has a second advance mechanism which is journalled in the tubular bar, wherein the tubular bar is designed as a piston rod of a first piston which is individually displaceable by a fluid in the pistol; and wherein the second advance mechanism is individually displaceable by a second piston, which is charged by the fluid and which ejects the displacer bar; with the two pistons being excitable with the fluid, which is under pressure, via a control device in the pistol; whereby the displacements of the two pistons relative to their cylinders are added for one large stroke.

2. Pistol in accordance with claim 1 wherein the fluid is a gas.

3. Pistol in accordance with claim 2 including a reservoir in the pistol for the gas.

4. Pistol in accordance with claim 1 wherein the second piston is blocked until the first piston has reached a predetermined front end position.

5. Pistol in accordance with claim 4 wherein the displacer bar is blocked in the ejection piston in such a manner that it punctures the ejection piston only at a predetermined breaking-loose force.

6. Pistol in accordance with claim 4 wherein the second piston can be charged with pressure only when the first piston has reached its predetermined front end position.

7. Pistol in accordance with claim 1 wherein the control device has a trigger bow which acts on a control slider for metering the fluid which is under pressure.

8. Pistol in accordance with claim 7 wherein the control slider covers off a tube piece with a blocking region and with a region with individual bores which can be brought one after the other into the fluid flow via the trigger bow in order to increase the ejection speed at the first piston step-wise.

9. Pistol in accordance with claim 8 wherein an increasing restoring force can be felt at the trigger bow with the increasing of the through-flow cross-section for the fluid flow.

10. Pistol in accordance with claim 9 wherein a first weak restoring spring is effective in the region of a predetermined smallest through-flow cross-section; and wherein a stiffer, second restoring spring is effective in the region with a greater through-flow cross-section.

11. Pistol in accordance with claim 8 wherein, when the trigger bow is not actuated, a connection line between the control slider and the first piston is ventilated by the control slider and an inflow line from a gas reservoir to the control slider is blocked.

12. Pistol in accordance with claim 5 including a differential piston which acts on the second piston and is journalled inside the first piston as a third piston in order to produce via its greater piston surface a greater breaking-loose force than can be produced with the second piston.

13. Pistol in accordance with claim 5 wherein the displacer bar is blocked in an axial direction through a membrane in the aperture of the ejection piston, the membrane being perforable at a predetermined breaking-loose force of the displacer bar in order to free the way for the latter in the ejection direction.

14. Pistol in accordance with claim 5 including a flap arranged in the aperture of the ejection piston which hinders the bone cement from flowing out and which frees the way for movement of the displacer bar in the ejection direction.

15. Pistol in accordance with claim 3 wherein the reservoir comprises a replaceable cartridge filled with one of $CO_2$ or $NO_2$.

16. Pistol for dispensing bone cement from a syringe which is attachable to the pistol and has a cylindrical portion terminating in a reduced cross-section neck through which fluid can be ejected and an ejection piston that is movable in the cylinder, the pistol comprising a first piston coupled to a tubular bar having a free end engageable with the ejection piston; a source of pressurized fluid and a control device fluidly coupled thereto for charging-the first piston with a pressurized fluid; a displacer bar axially movable disposed in the tubular bar and having an end extendable through the ejection cylinder for extending the displacer bar into the neck of the syringe; and a second piston operatively coupled with the displacer bar for axially moving the displacer bar relative to the tubular bar and thereby extending the displacer bar beyond the end of the tubular bar into the neck of the syringe; the control device being fluidly connected with and operative for charging the second piston with pressurized fluid independently of the first piston so that the first and second-pistons can be activated independently of each other.

17. Pistol for use with a syringe having a cylinder terminating in a reduced cross-section neck through which fluid can be ejected and an ejection piston including a central, axially oriented, closable through aperture and being movably disposed in the cylinder of the syringe, the pistol comprising a housing and a telescopic actuator for reciprocating the ejection piston in the syringe and forcing fluid through the neck out of the syringe, the telescopic actuator comprising a first piston coupled to a tubular piston rod and reciprocably arranged in the pistol housing, a forward end of the tubular piston rod being engageable with the ejection piston for moving the ejection piston towards the neck of the syringe, a second piston coupled to a second piston rod axially movably arranged within the tubular piston rod, the second piston rod being extendable through the aperture in the ejection piston for movement toward and into the neck of the syringe; and fluid flow control means operatively coupled with the first and second pistons for independently charging the first and second pistons with a pressurized fluid and therewith independently activating the pistons so that, upon activation of the second piston by the control means, the second piston moves the second piston rod relative to the tubular piston rod.

* * * * *